//  US006551284B1

United States Patent
Greenberg et al.

(12) 
(10) Patent No.: US 6,551,284 B1
(45) Date of Patent: Apr. 22, 2003

(54) CATHETER HUB ATTACHMENT ASSEMBLY

(75) Inventors: Robert S. Greenberg, Glenelg, MD (US); Carol M. Gentry, Havre De Grace, MD (US)

(73) Assignee: Easy-Stik, LLC, Glenelg, MD (US)

( * ) Notice: Subject to any disclaimer, the term of this patent is extended or adjusted under 35 U.S.C. 154(b) by 0 days.

(21) Appl. No.: 09/377,107

(22) Filed: Aug. 19, 1999

(51) Int. Cl.[7] ................................................ A61M 5/32
(52) U.S. Cl. ...................................... 604/180; 604/174
(58) Field of Search ................................ 604/174, 180, 604/264

(56) References Cited

U.S. PATENT DOCUMENTS

| | | | |
|---|---|---|---|
| 3,630,195 A | | 12/1971 | Santomieri |
| 3,834,380 A | * | 9/1974 | Boyd ........................ 128/133 |
| 3,863,631 A | * | 2/1975 | Baldwin |
| 4,324,236 A | * | 4/1982 | Gordon et al. .......... 128/214 R |
| 4,460,356 A | | 7/1984 | Moseley |
| 4,484,913 A | * | 11/1984 | Swauger ..................... 604/179 |
| 4,563,177 A | * | 1/1986 | Kamen ........................ 604/177 |
| 4,627,842 A | | 12/1986 | Katz |
| 4,690,675 A | | 9/1987 | Katz |
| 4,737,143 A | | 4/1988 | Russell |
| 4,822,342 A | | 4/1989 | Brawner |
| 5,137,520 A | * | 8/1992 | Maxson |
| 5,215,532 A | | 6/1993 | Atkinson |
| 5,300,037 A | * | 4/1994 | Delk et al. .................. 604/180 |
| 5,470,320 A | * | 11/1995 | Tiefenbrun |
| 5,520,656 A | * | 5/1996 | Byrd ........................... 604/180 |
| 5,776,220 A | * | 7/1998 | Moenning ................... 606/213 |
| 5,797,884 A | * | 8/1998 | Byrd ........................... 604/180 |

* cited by examiner

*Primary Examiner*—Henry Bennett
*Assistant Examiner*—Nihir Patel
(74) *Attorney, Agent, or Firm*—Nixon & Vanderhye PC

(57) ABSTRACT

A catheter assembly is provided that has an adhesive on an undersurface of the hub thereof, which is revealed following catheter insertion so that the catheter hub can be secured to the skin while maintaining universal precautions. A protective covering is applied over the adhesive material to preclude adhesion of the catheter hub to the medical practitioner's gloves or premature adhesion to the patient's skin. Once the catheter has been properly positioned, the protective covering is removed by gripping a pull tab, which projects proximally, away form the inserted catheter tip and beyond the catheter hub. Pulling the tab everts the protective cover by folding the cover back over itself to gradually reveal the adhesive surface of the skin. The catheter hub is pressed firmly to the skin in order to create an effective adherence. If deemed necessary or desirable, additional tape or other securing devices may be applied to the adhered catheter hub.

20 Claims, 4 Drawing Sheets

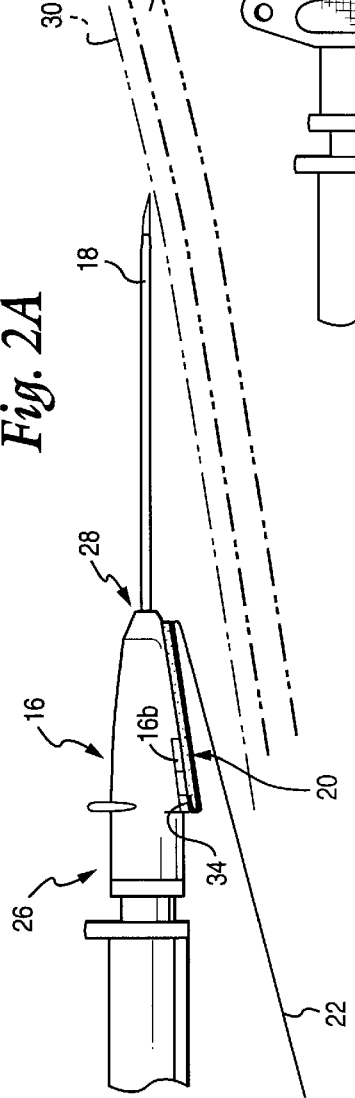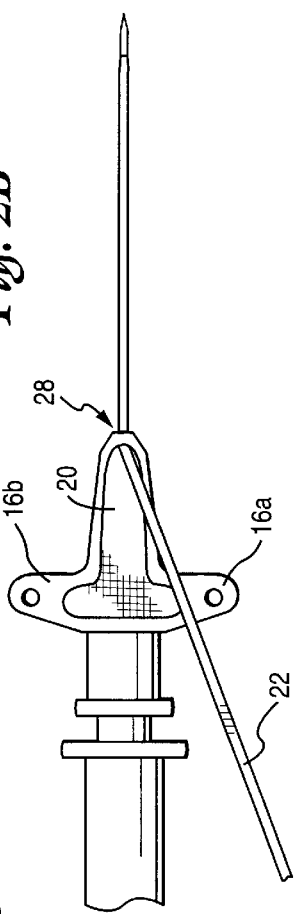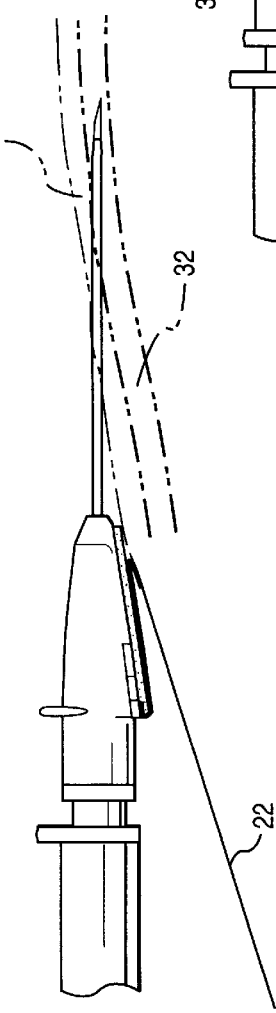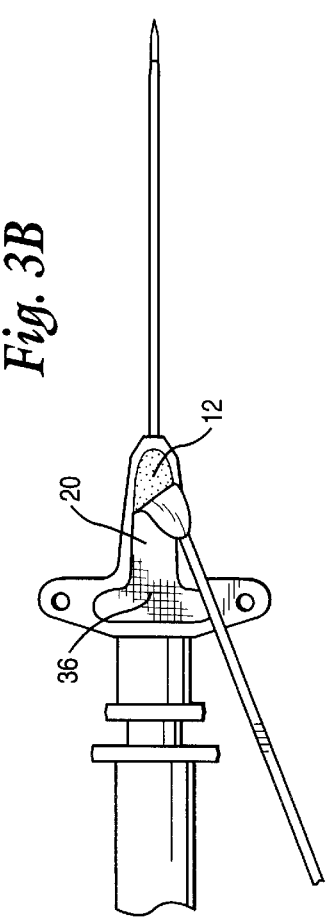

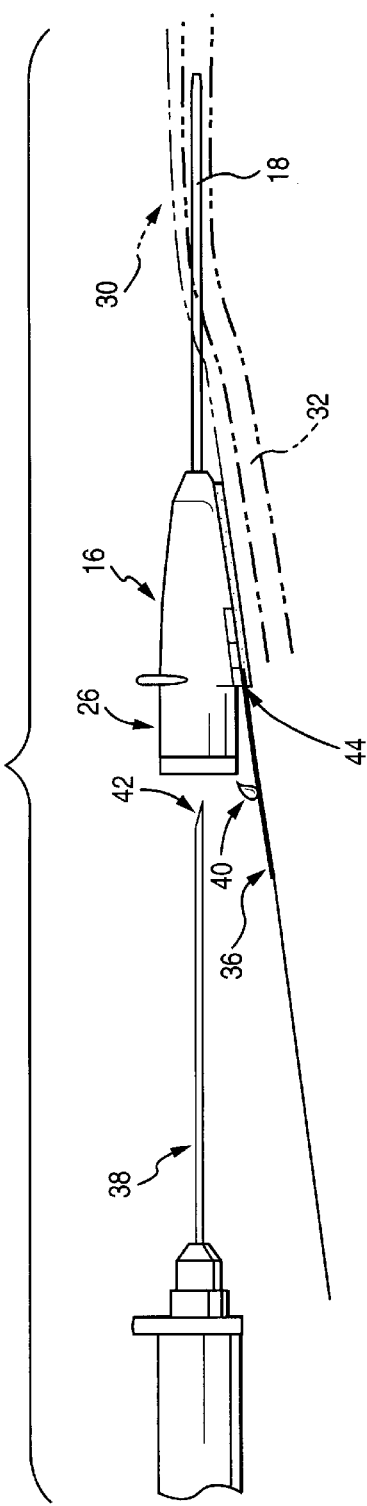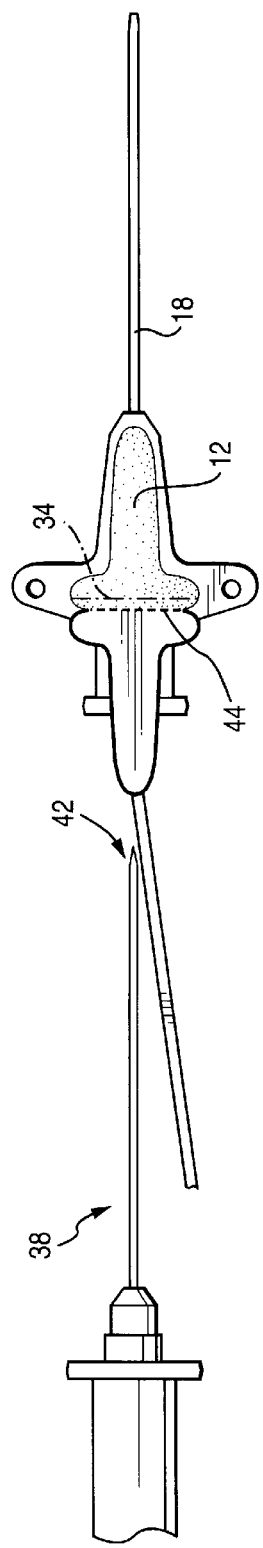
Fig. 4A
Fig. 4B

CATHETER HUB ATTACHMENT ASSEMBLY

BACKGROUND OF THE INVENTION

1. Field of the Invention

The present invention relates to catheters and, more particularly, to an improved intravascular catheter having a hub which may be easily secured to the skin while maintaining universal precautions.

2. Description of the Related Art

When a vascular catheter is placed, for example for intravenous administration of fluids, a combined catheter and needle is used to create the vascular puncture after which the needle is removed and the hub of the remaining catheter attached to a source of infusion liquid. It is necessary to stabilize the catheter in relation to the blood vessel to prevent movement of the catheter to preclude catheter withdrawal, undesirable additional blood vessel punctures and the like. The catheter hub is typically stabilized by taping the hub and associated tube fittings to the patient's skin in the area adjacent the vessel puncture.

Universal precautions, i.e., the use of gloves, while placing intravascular catheters has made the process of securing these catheters complicated. Indeed, in general, it is difficult to apply sticky tape to the skin while wearing gloves. In addition, the extra movement needed to reach for and to apply such tape risks the loss of the unsecured catheter. This is particularly true where the catheter has been placed in a child. As a result, it is not uncommon for universal precautions to be broken, i.e., gloves taken off, so that the catheter can be secured, but without skin protection, or for tape to be applied, as best as possible, many times with the loss of the proper position of the catheter.

There have been prior attempts to address the foregoing problem of stabilization of an inserted needle or catheter immediately following vein puncture. This has typically been accomplished by providing an adhesive surface on the undersurface of wings provided on the catheter hub. Such intravenous needle assemblies are shown, for example, in U.S. Pat. Nos. 4,324,236 and 4,627,842. A difficulty encountered with such prior art products, however, is that the protective covering on the adhesive must be removed before the needle is inserted into the vein so that it may be thereafter adhered to the skin surface. Providing an adhesive surface that is exposed before vein puncture, however, risks premature adhesion to the skin and/or adhesion to the medial care provider's gloves.

SUMMARY OF THE INVENTION

The catheter structure provided in accordance with the invention was designed to provide an easy way to secure the catheter hub to the skin while maintaining universal precautions and avoiding premature adhesion to the skin surface. In the presently preferred embodiment, the invention is applied to a vascular catheter.

In accordance with the invention, an adhesive layer is provided on the underside of a catheter hub. A protective covering is applied over the adhesive layer to preclude adhesion of the catheter hub to the medical practitioner's gloves or premature adhesion to the patient's skin. This protective cover is maintained on the adhesive until the catheter has been placed, e.g., in a blood vessel. Once the catheter has been properly positioned, the protective covering is removed. This is accomplished in a presently preferred embodiment by gripping a pull tab, which preferably projects proximally, away form the inserted catheter tip. The pull tab is thus available to be pulled to peel back the protective cover by folding the cover back over itself and pulling it proximally from the inserted catheter tip to reveal the sticky surface of the skin. The catheter hub is pressed firmly to the skin in order to create an effective adherence. If deemed necessary or desirable, additional tape or securing devices may be applied to the adhered catheter hub.

In one embodiment, the exposed surface of the protective covering has a thin layer of absorbent material so that, as the protective cover is everted to expose the adhesive surface, it defines a splash-absorbent plate to protect the patient's skin from being soiled with blood, particularly when the introducer needle is removed.

In accordance with a further alternate embodiment of the invention, when the protective cover is everted and peeled back to expose the adhesive surface, the peel back action does not entirely remove the protective cover from the hub. Instead, an additional and potentially greater force must be applied to fully remove the cover from the catheter hub. This alternative may be advantageously employed to ensure that the protective cover remains in position to catch any spillage, particularly upon introducer needle removal.

BRIEF DESCRIPTION OF THE DRAWINGS

These, as well as other objects and advantages of this invention, will be more completely understood and appreciated by careful study of the following more detailed description of the presently preferred exemplary embodiments of the invention taken in conjunction with the accompanying drawings, in which:

FIG. 2A is a schematic elevational view of a vascular catheter in accordance with the invention, ready for insertion into a vein;

FIG. 2B is a schematic bottom view of the vascular catheter of FIG. 2A;

FIG. 3A is a schematic elevational view of the vascular catheter showing a first stage of protective cover removal;

FIG. 3B is a schematic bottom view of the vascular catheter of FIG. 3A;

FIG. 4A is a schematic elevational view of the vascular catheter showing a second stage of protective cover removal;

FIG. 4B is a schematic bottom view of the vascular catheter of FIG. 4A;

DETAILED DESCRIPTION OF THE PRESENTLY PREFERRED EXEMPLARY EMBODIMENTS

Figure 1:
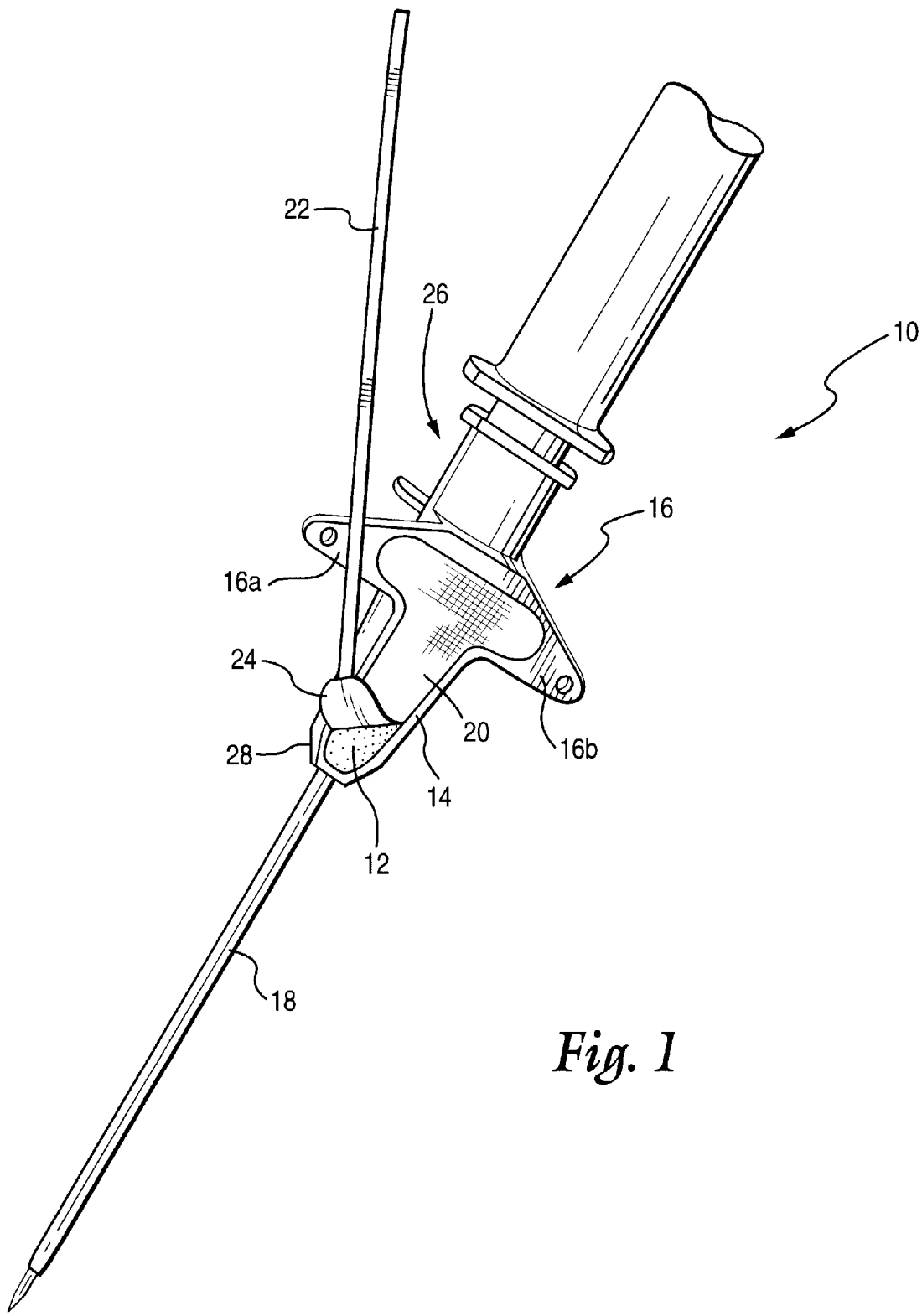
FIG. 1 is a bottom perspective view of a vascular catheter provided in accordance with the invention.
Figure 5A:
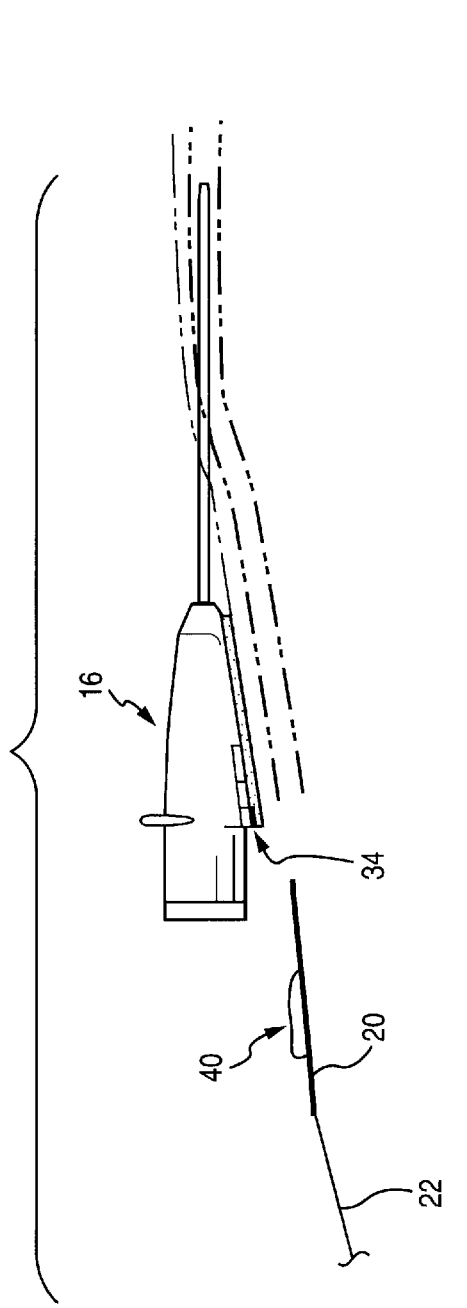
FIG. 5A is a schematic elevational view of the vascular catheter with protective cover removed.
Figure 5B:
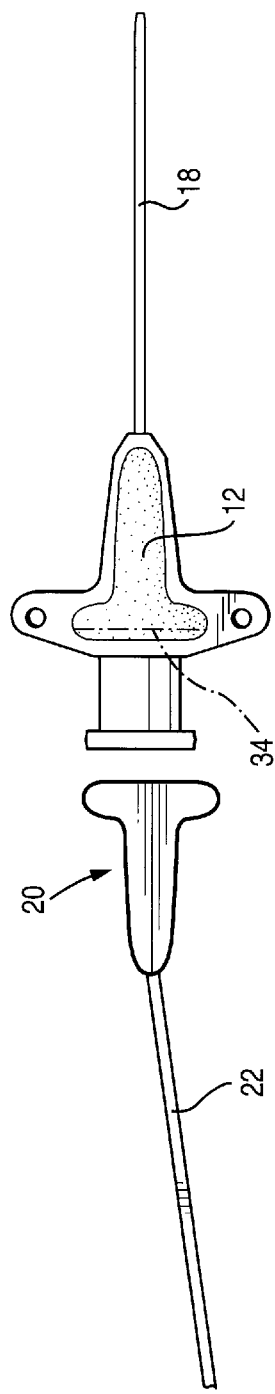
FIG. 5B is a schematic bottom view of the vascular catheter of FIG. 5A.

Referring to FIG. 1, there is shown therein the underside of a catheter hub attachment assembly 10 provided in accordance with a first exemplary embodiment of the invention. As illustrated, an adhesive layer 12 is provided on the undersurface 14 of the hub 16 of an intravascular catheter 18. In the illustrated embodiment the catheter hub 16 is of a generally conventional configuration, having a pair of laterally projecting wings 16a and 16b for stabilizing the hub on the surface of the patient's skin upon insertion of the catheter 18 into the blood vessel. Moreover, for stability and to improve adhesion, the undersurface 14 of the hub 16, including the wings 16a and 16b, is preferably generally flat.

The adhesive layer 12 may be defined by providing an adhesive material directly on the undersurface 14 of the catheter hub 16 or by applying a substrate having adhesive coated surfaces, i.e., double sided tape, to the undersurface 14 of the catheter hub 16 so that one of the adhesive surfaces can be exposed for adhesion to the skin. The exposed adhesive surface has a protective cover 20 generally coextensively applied thereto.

For removing the protective cover 20 from the adhesive surface, a pull tab or string 22 is provided to extend, at least at the time of removal, proximally from the distal end 24 of the protective cover 20. The pull tab 22 may be continuous with, and formed from the same material as, the protective cover 20. In the alternative, the pull tab or string 22 may be a separate component of the same or different material securely attached to the distal end 24 of the cover 20 so that when the pull tab 22 is pulled in a proximal direction, away from the catheter 18, the protective cover 20 is everted and peeled back to expose the adhesive surface 12 to the skin. The protective cover eversion process has just begun in the illustration of FIG. 1.

As illustrated in FIGS. 1, 2A and 2B, the proximally extending pull tab 22 is preferably accessible to the right or to the left of the proximal end 26 of the catheter hub 16 so that it can be located, gripped, and pulled without interfering with access to the proximal end 26 of the catheter hub 16. While the pull tab need not be preformed to project in any particular direction, since it can be grasped and pulled from substantially any disposition about the catheter hub 16, the tab 22 may be preformed and/or folded to project at an angle of between about 0 and 90°, and more preferably, at an angle of between about 30 and 45° from the longitudinal axis of the hub. As will be apparent, even when the tab projects to the side, the pull tab 22 allows for and effects substantially longitudinal eversion and removal of the protective cover 20, gradually from the distal end 28 of the hub 16 to the proximal end 26 thereof, so as to gradually expose the adhesive surface 12 to the skin 30 for adhesion.

FIGS. 2A–5A illustrate the removal of the protective cover. In FIGS. 2A and 2B that the catheter insertion assembly 10 is ready for vessel puncture with the protective cover 20 fully covering the adhesive surface 12 and the pull tab or string 22 extending proximally either axially of the hub 16 or slightly to the right or to the left, for easy access to pull the same once the puncture of the vessel 32 has been achieved. As shown in FIGS. 2A and 2B, the most proximal end 34 of the protective cover 20 may be folded under and adhered to the catheter hub 16, either under or on the adhesive material 12. The proximal end of the protective cover 20 is folded under for providing for two stage protective cover 20 removal, as discussed in more detail below.

FIG. 3A illustrates the intravenous catheter assembly 10 following vessel puncture and the beginning of removal of the protective cover 20. As shown, gradual pulling of the pull tab 22 everts the distal end 24 of the protective cover 20 to expose the adhesive 12 on the undersurface 14 of the hub 16. Eversion and removal of the protective cover 20 can thus be achieved without lifting or other substantial displacement of the catheter hub.

In accordance with a presently preferred embodiment of the invention, the exposed surface 36 of the protective cover 20 is defined by an absorbent material. Absorbent as used herein means a material or media adapted to receive and retain a fluid or semi-fluid material and may be, but is not limited to, a hydrophilic material. Accordingly, in the event a modest amount of blood 40 spills from the catheter hub 16 or needle tip 42, when the introducer needle 38 is removed, the absorbent surface 32 of the protective cover 20 receives and retains the blood 40 thereon. Thus, the fully everted protective cover 20 defines a splash-absorbent plate to protect the skin 30 from being soiled with blood 40, particularly when the introducer needle 38 is removed.

As shown in FIG. 4A, in accordance with a presently preferred embodiment, when the protective cover 20 is fully everted, the protective cover 20 nonetheless remains engaged with the catheter hub 16 via the pre-folded end portion 34 which remains, e.g., adhered to the catheter hub 16.

As a result, an additional, and potentially greater, force must be applied to the protective cover 20 to remove it from the hub 16. This additional force, however, should not be greater than and is preferably substantially less than the adhesive force that secures the catheter hub to the patient's skin 30, so as to ensure that the catheter 18 will not be inadvertently disengaged from its proper vein placement. The required additional force is also substantially less than a force that would risk detachment of the pull tab 22 from the cover distal end 24. In the presently preferred embodiment, there is a line of weakness at the juncture of the proximal end portion 34 to the remainder of the protective cover 20 such that with a modest additional tug on the pull tab 22, the protective cover becomes fully detached from the hub. The line of weakness may be, for example, a region of the protective cover that is preformed or scored to have a reduced thickness. In the illustrated embodiment, that line of weakness is a perforated line 44.

As will be appreciated from the foregoing, the vascular catheter assembly disclosed herein provides an easy way to secure an intravascular catheter to the skin while maintaining universal precautions and avoiding premature adhesion to the skin surface.

As will be further appreciated from the foregoing, although the invention has been described with reference to a vascular catheter, the adhesive layer and protective cover embodying the invention could be provided on the hub of any of a variety of cannulas, where it is desirable to stabilize the cannula in relation to the point of insertion, to prevent movement of the cannula to preclude cannula withdrawal.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An assembly comprising:
   a hub component having a longitudinal axis, a distal end, a proximal end, and an axial bore defined therethrough;
   a cannula extending axially from said distal end of said hub component and having at least one bore defined therethrough;
   an adhesive material provided on at least a portion of an undersurface of said hub component;
   a protective cover overlying said adhesive material, said protective cover comprising a flexible sheet and having a distal end portion disposed adjacent said distal end of said hub component; and
   a pull tab extending from said distal end portion of said protective cover and having a length greater than a length of said protective cover, whereby said pull tab can be disposed so as to extend from said distal end portion of said protective cover proximally, beyond said proximal end of said hub component, for being manually grasped and pulled, following insertion of said cannula into a patient, to generally longitudinally evert said protective cover to expose said adhesive material to the patient's skin proximate a point of said insertion.

2. An assembly as in claim 1, wherein said pull tab has a transverse width substantially less than a transverse width of said protective cover.

3. An assembly as in claim 1, wherein said hub component includes a hub main body and a pair of laterally projecting wing elements for stabilizing said hub main body on the surface of the patient's skin upon insertion of said cannula.

4. An assembly as in claim 3, wherein said hub main body is integrally formed with said wing elements.

5. An assembly as in claim 3, wherein said adhesive material is provided on an undersurface of said wing elements.

6. An assembly as in claim 5, wherein said adhesive material is further provided on an under surface of said hub main body.

7. An assembly as in claim 1, wherein said hub component includes a generally flat portion defined on an undersurface thereof for being disposed in opposed facing relation to the patient's skin, said adhesive material being provided on said generally flat portion of said hub component.

8. An assembly as in claim 7, wherein said cannula comprises a vascular catheter for insertion into a blood vessel, and said hub component includes a hub main body and a pair of laterally projecting wing elements for stabilizing said hub main body on the surface of the patient's skin upon insertion of said vascular catheter into said blood vessel.

9. An assembly as in claim 8, wherein said hub main body is integrally formed with said wing elements.

10. An assembly as in claim 8, wherein said flat portion comprises the undersurfaces of said wing elements.

11. An assembly as in claim 1, wherein said protective cover includes a first surface for being disposed in opposed facing relation to said adhesive material and providing for release from said adhesive material while substantially an entirety of said adhesive material remains disposed on said hub component, and a second surface, said second surface comprising an absorbent material.

12. An assembly as in claim 1, wherein said cannula comprises a vascular catheter for insertion into a blood vessel, and said protective cover also has a main body portion and a proximal end portion, each having first and second surfaces, said first surface of said main body portion of said protective cover being disposed in opposed facing relation to the patient's skin following insertion of said vascular catheter into a blood vessel, said proximal end portion of said protective cover being folded under said main body portion of said protective cover such that said first surface thereof is facing the hub component and secured with respect thereto.

13. An assembly as in claim 12, further comprising a line of weakness at a juncture of said proximal end portion to said main body portion of protective cover, whereby said protective cover can be severed at said line of weakness so as to separate said proximal end portion from said main body portion of said protective cover.

14. An assembly as in claim 13, wherein said line of weakness is a perforated line.

15. An assembly as in claim 1, wherein said cannula comprises a vascular catheter.

16. An assembly as in claim 15, further comprising a tissue penetrating needle structure removably disposed in said catheter for blood vessel puncture to insert said catheter into the blood vessel.

17. A method for securing a cannula assembly with respect to a patient's skin comprising:

providing a cannula assembly including:
a hub component having a longitudinal axis, a distal end, a proximal end, and an axial bore defined therethrough;
a cannula extending axially from said distal end of said hub component and having at least one bore defined therethrough;
an adhesive material provided on at least a portion of an undersurface of said hub component;
a protective cover overlying said adhesive material, said protective cover comprising a flexible sheet and having a distal end portion disposed adjacent said distal end of said hub component; and
a pull tab extending from said distal end portion of said protective cover and having a length greater than a length of said protective cover;

inserting said cannula into a patient so that a distal end thereof is disposed within the patient and said hub component is disposed adjacent the surface of the skin in proximity to a point of said insertion, with said undersurface thereof in opposed facing relation to the skin;

manually grasping said pull tab and pulling said pull tab so as to displace said distal end portion of said protective cover out of engagement with said adhesive material;

continuing said pulling so as to evert said protective cover to progressively reveal more proximal portions of said adhesive material until said adhesive material is substantially fully exposed to and engaged with the patient's skin proximate said point of insertion.

18. A method as in claim 17, wherein said cannula is a vascular catheter and said protective cover also has a main body portion and a proximal end portion, each having first and second surfaces, said first surface of said main body portion of said protective cover being disposed in opposed facing relation to the patient's skin following insertion of said vascular catheter into a blood vessel, said proximal end portion of said protective cover being folded under said main body portion of said protective cover such that said first surface thereof is facing said hub component and secured with respect thereto, wherein there is a line of weakness at a juncture of said proximal end portion to said main body portion of protective cover, whereby said protective cover can be severed at said line of weakness, and wherein the method further comprises disengaging said main body portion of said protective cover from said proximal end portion thereof.

19. A method as in claim 17, wherein said protective cover includes a first surface for being disposed in opposed facing relation to said adhesive material and providing for release from said adhesive material while substantially an entirety of said adhesive material remains disposed on said hub component, and a second surface, said second surface comprising an absorbent material, and wherein the method further comprises receiving and absorbing at least some fluid which spills from said hub component following cannula insertion.

20. A method as in claim 17, wherein said cannula comprises a vascular catheter and said assembly further comprises a tissue penetrating needle structure removably disposed in said catheter for blood vessel puncture.

* * * * *